(12) United States Patent
Bondavalli et al.

(10) Patent No.: US 7,589,086 B2
(45) Date of Patent: Sep. 15, 2009

(54) SUBSTITUTED PYRAZOLO[3,4-D]PYRIMIDINES AS ANTI-TUMOR AGENTS (75) Inventors: Francesco Bondavalli, Siena (IT); Maurizio Botta, Siena (IT); Olga Bruno, Siena (IT); Fabrizio Manetti, Siena (IT); Silvia Schenone, Siena (IT); Fabio Carraro, Siena (IT)

(73) Assignee: Universita degli Studi di Siena, Siena (IT)

( * ) Notice: Subject to any disclaimer, the term of this patent is extended or adjusted under 35 U.S.C. 154(b) by 40 days.

(21) Appl. No.: 10/558,553

(22) PCT Filed: May 26, 2004

(86) PCT No.: PCT/IT2004/000303

§ 371 (c)(1), (2), (4) Date: Aug. 14, 2006

(87) PCT Pub. No.: WO2004/106340

PCT Pub. Date: Dec. 9, 2004

(65) Prior Publication Data

US 2007/0010510 A1   Jan. 11, 2007

(30) Foreign Application Priority Data

May 28, 2003 (IT) .............................. RM03A0263
May 28, 2003 (IT) .............................. RM03A0264

(51) Int. Cl.
C07D 487/04 (2006.01)
A61K 31/519 (2006.01)
C07D 403/04 (2006.01)
A61K 31/551 (2006.01)
A61K 31/5355 (2006.01)
C07D 413/04 (2006.01)
A61P 35/04 (2006.01)

(52) U.S. Cl. ............... 514/217.06; 540/600; 514/234.5; 514/262.1; 544/118; 544/262

(58) Field of Classification Search ................. 544/262, 544/118; 514/262.1, 234.5, 217.06; 540/600
See application file for complete search history.

(56) References Cited

U.S. PATENT DOCUMENTS 5,981,533 A    11/1999    Traxler et al.

OTHER PUBLICATIONS

Schenone et. al. (Bioorganic and Medicinal Chemistry Letters, 2004, 14(10), 2511-2517.*
Schenone et. al. (European Journal of Medicinal Chemisty Letters, 2004, 39(2), 153-160.*
Schenone et. al. (Journal of Medicinal Chemisty Letters, 2004, 47(7), 1595-1598).*
PCT International Search Report, dated Jan. 17, 2005, for Universita Degli Studi Di Siena, et al., International Application No. PCT/IT2004/000303, May 26, 2004.
Dumas. J. Protein kinase inhibitors: emerging pharmacophores 1997-2000. Expert Opinion on Therapeutic Patents, Ashley Publications. GB, vol. 11, No, 3, 2001, pp. 405-429.
Hayashi, E. Anti-tumor Activity of Eighty Four Synthesized N-heteroaromatic Compounds. Yakugaku Zasshi—Journal of the Pharmaceutical Society of Japan, Nihon Yakugakkai, Tokyo, JP, vol. 97, No. 9, 1977, pp. 1022-1033.

* cited by examiner

*Primary Examiner*—Brenda L Coleman
*Assistant Examiner*—Susanna Moore
(74) *Attorney, Agent, or Firm*—Law Offices of Albert Wai-Kit Chan, PLLC

(57) ABSTRACT

The present invention provides a compound of pyrazolo[3,4-d]pyrimidine having the formula

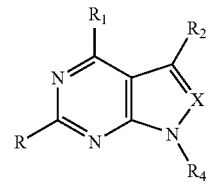

(I)

wherein:
X=N;
R=H, alkylthio, or aminoalkylthio;
$R_1$=NHcyclopropyl, $NHC_3H_7$, $NHC_4H_9$, $N(CH_2CH_3)_2$, $NHCH_2CH_2OC_2H_5$, 1-pyrrolidinyl, 1-piperidinyl, 4-morpholinyl, NHcyclohexyl, 1-hexahydroazepinyl, $NHCH_2C_6H_5$, or $NHCH_2CH_2C_6H_5$;

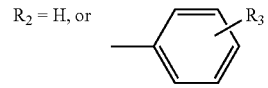

wherein $R_3$=H, halogen, or alkyl

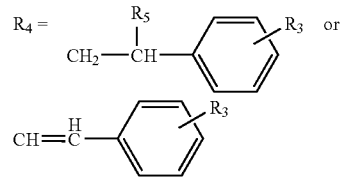

and
$R_5$=Cl, Br or OH.

14 Claims, 4 Drawing Sheets

Example of a synthetic pathway for compounds 1-5. Figure 1.

SUBSTITUTED PYRAZOLO[3,4-D]PYRIMIDINES AS ANTI-TUMOR AGENTS

CROSS-REFERENCE TO RELATED APPLICATIONS

This application is a National Phase application of International Application No. PCT/IT2004/000303, filed May 26, 2004, which claims priority of Italian patent application Nos. RM2003A000263, filed May 28, 2003, and RM2003A00264, filed May 23, 2003. The contents of the preceding applications are hereby incorporated in their entireties by reference into this application.

Throughout this application, various publications are referenced. Disclosures of these publications in their entireties are hereby incorporated in their entireties by reference into this application in order to more fully describe the state of the art to which this invention pertains.

BACKGROUND OF THE INVENTION

The present patent concerns 4-substituted derivatives of pyrazolo[3,4-d]pyrimidine and pyrrolo[2,3-d]pyrimidine. In addition, the patent concerns the use of compounds, herein described, as agents especially, but not limited, for the therapy of tumours and leukaemia, their use for preparing pharmaceutical compositions, methods for the synthesis of compounds and their intermediates.

Over the past three decades, neoplastic diseases have been the second most common cause of death among western population, and the incidence rates have been increasing over time.[1] Meanwhile, if the survival rates of cancer patients are increasing substantially, the incidence rates are still very high. The phenotype shift from the standard to the neoplastic one is a substantially complex biological event, involving many alterations in cell physiology. Among them, transduction factor over expression has a critical role, and one of the most studied and interesting modifications are those involving over expression of Src tyrosine kinase (TK).[2] Such TK is the prototype member of the non-receptor Src family of protein tyrosine kinases (PTK).[3] Src is activated following engagement of many different classes of cellular receptors and participates as a convergence point in different signalling pathways.[4,5] In this regard, Src is a critical component of the signalling cascades initiated by TK-linked receptors, such as the epidermal growth factor receptor (EGFR) and G-protein coupled receptors, and is directly associated with, and may regulate signalling via, the EGFR and HER-2/neu PTK receptor,[6,7] both of which are involved in cancer. Finally, Src over expression and activation has been correlated with a large number of growth-regulatory processes where Src participates. The process of activation of Src is mediated by the phosphorylation of the tyrosine 416; on this basis, inhibitors of Src phosphorylation process may halt uncontrolled tumour cell growth and play an important role as new therapeutic agents for the treatment of cancer.

BRIEF SUMMARY OF THE INVENTION

The authors have designed and synthesized a new class of pyrazolo[3,4-d]pyrimidine derivatives. They have also found that some of such compounds were inhibitors of cell proliferation in A431, 8701-BC and leukaemia cell lines. Thus, the new compounds could be considered as potential anti tumour and antileukaemic agents. Therefore it is an object of the invention a 4-substituted derivative of pyrazolo[3,4-d]pyrimidine or pyrrolo[2,3-d]pyrimidine having the formula

(I)

wherein:

X=CH or N;

R=H, alkylthio, or aminoalkylthio;

$R_1$=NHcyclopropyl, or $NHC_3H_7$, or $NHC_4H_9$, or $N(CH_2CH_3)_2$, or $NHCH_2CH_2OC_2H_5$, or 1-pyrrolidinyl, or 1-piperidinyl, or 4-morpholinyl, or NHcyclohexyl, or 1-hexahydroazepinyl, or $NHCH_2C_6H_5$, or $NHCH_2CH_2C_6H_5$;

where $R_3$=H, halogen, alkyl.

$R_5$=Cl, Br or OH.

Preferably X=N; R=H or $SCH_3$, or $SC_2H_5$; $R_1$=$NHC_3H_7$, or $NHC_4H_9$, or $N(CH_2CH_3)_2$, or $NHCH_2CH_2OC_2H_5$, or 1-pyrrolidinyl, or 1-piperidinyl, or 4-morpholinyl, or NHcyclohexyl, or 1-hexahydroazepinyl, or $NHCH_2C_6H_5$, or $NHCH_2CH_2C_6H_5$;

$R_2$=H; $R_3$=H;

$R_5$=Cl, Br, OH.

Preferably X=N, R=$SCH_3$, $R_1$ is one of the following residues: $NHC_4H_9$, or 1-piperidinyl, or 4-morpholinyl, or $NHCH_2C_6H_5$, or $NHCH_2CH_2C_6H_5$. $R_2$=$R_3$=H, $R_4$=2-chloro-2-phenylethyl.

Preferably X=N, R=SC$_2$H$_5$, R$_1$ is one of the following residues: NHC$_3$H$_7$, or NHC$_4$H$_9$, or NHCH$_2$C$_6$H$_5$. R$_2$=R$_3$=H, R$_4$=2-chloro-2-phenylethyl.

Preferably X=N, R=H, R$_1$ is one of the following residues: NHC$_4$H$_9$, or NHcyclohexyl. R$_2$=R$_3$=H, R$_4$=2-bromo-2-phenylethyl.

Preferably X=N, R=H, R$_1$ is one of the following residues: 1-piperidinyl, or NHCH$_2$C$_6$H$_5$, or NHCH$_2$CH$_2$C$_6$H$_5$. R$_2$=R$_3$=H, R$_4$=2-hydroxy-2-phenylethyl.

Preferably X=N, R=H, R$_1$ is one of the following residues: NHCH$_2$CH$_2$OC$_2$H$_5$, or NHCH$_2$C$_6$H$_5$, or NHCH$_2$CH$_2$C$_6$H$_5$. R$_2$=R$_3$=H, R$_4$=styryl.

In one embodiment of the invention, the compound of the invention is used as medicament, preferably as an anti-tumour and/or anti-leukaemia agent.

It is another object of the invention a pharmaceutical composition comprising at least one of the compounds of the invention or a pharmaceutically acceptable salt thereof, and suitable excipients and/or diluents.

Compounds of the invention or their salts may be administered as pure or as pharmaceutical formulations, i.e. suitable for parenteral, oral, or rectal administrations. Each of said formulations may contain excipients and/or fillers and/or additives and/or binders, coatings and/or suspending agents and/or emulsifying agents, preserving and/or control release agents, suitable for the selected pharmaceutical form.

BRIEF DESCRIPTION OF THE DRAWINGS

The invention shall be described with reference to following Figures.

DETAILED DESCRIPTION OF THE INVENTION

EXAMPLE 1

Chemistry: Materials and Methods for Synthesis

Compounds 1-2 (FIG. 1) were prepared starting from the ethyl ester of 5-amino-1-(2-hydroxy-2-phenylethyl)-1H-pyrazole-4-carboxylic acid 5, obtained following our reported procedure.[8] Reaction of 5 with benzoyl isothiocyanate in THF at reflux for 8 h yielded the intermediate 6, which was cyclized to the pyrazolo[3,4-d]pyrimidine 7 by treatment with 1M NaOH at 100° C. for 10 min, followed by acidification with acetic acid (80% yield). Alkylation of the thio group in position 6 with methyl or ethyl iodide in THF at reflux afforded the 6-thioalkyl derivatives 8, that were in turn treated with the Vilsmeier complex (POCl$_3$:DMF, 4 equiv) in CHCl$_3$ to obtain the dihalogenated compounds 9 bearing the chlorine atom both at the position 4 of the pyrimidine nucleus and the N1 side chain. Compounds 9 were purified in good yield by chromatography on Silica Gel column. Finally, regioselective substitution of the C4 chlorine atom with an excess of various amines afforded the desired compounds 1-2 in yields ranging between 60 and 80%. Notably, the chlorine atom at the side chain has never been substituted by the amine in spite of its benzylic position, as shown by the $^1$H NMR chemical shifts of the CH$_2$—CH side chain, which give an ABX complex pattern which it is similar to that of the starting material.

Reaction of 5 with formamide in excess at 190° C. for 8 h afforded the pyrazolo[3,4-d]pyrimidinone 10 which was purified by dissolving the crude in 2M NaOH, boiling with coal, followed by precipitation with acetic acid (yield 70%, m.p. 271-272° C.). Compound 11 was prepared in a yield of 44% following the Beal and Véliz[9] procedure by treatment of 10 with a mixture of HMPT/NBS in acetonitrile at −20° C. followed by addition of LiBr and refluxing. It is interesting to point out that the secondary OH on the side chain remained unaltered by this procedure, as shown by its $^1$H NMR spectrum. Treatment of 11 with morpholine, butylamine, or piperidine gave the desired compounds 3a-c.

Reaction of 10 at reflux with POCl$_3$ afforded the 1-styryl derivative 12 which was reacted with an excess of various amines in toluene to give 4a-d in good yield. Starting materials were purchased from Aldrich-Italia (Milan, Italy).

Melting points were determined with a Büchi 530 apparatus and are uncorrected. IR spectra were measured in KBr with a Perkin-Elmer 398 spectrophotometer. $^1$H NMR spectra were recorded in a (CD$_3$)$_2$SO solution on a Varian Gemini 200 (200 MHz) instrument. Chemical shifts are reported as δ (ppm) relative to TMS as internal standard, J in Hz. $^1$H patterns are described using the following abbreviations: s=singlet, d=doublet, t=triplet, q=quartet, sx=sextect, m=multiplet, br=broad. All compounds were tested for purity by TLC (Merk, Silica gel 60 F$_{254}$, CHCl$_3$ as eluant).

Analyses for C, H, N were within ±0.3% of the theoretical value.

Figure 1:
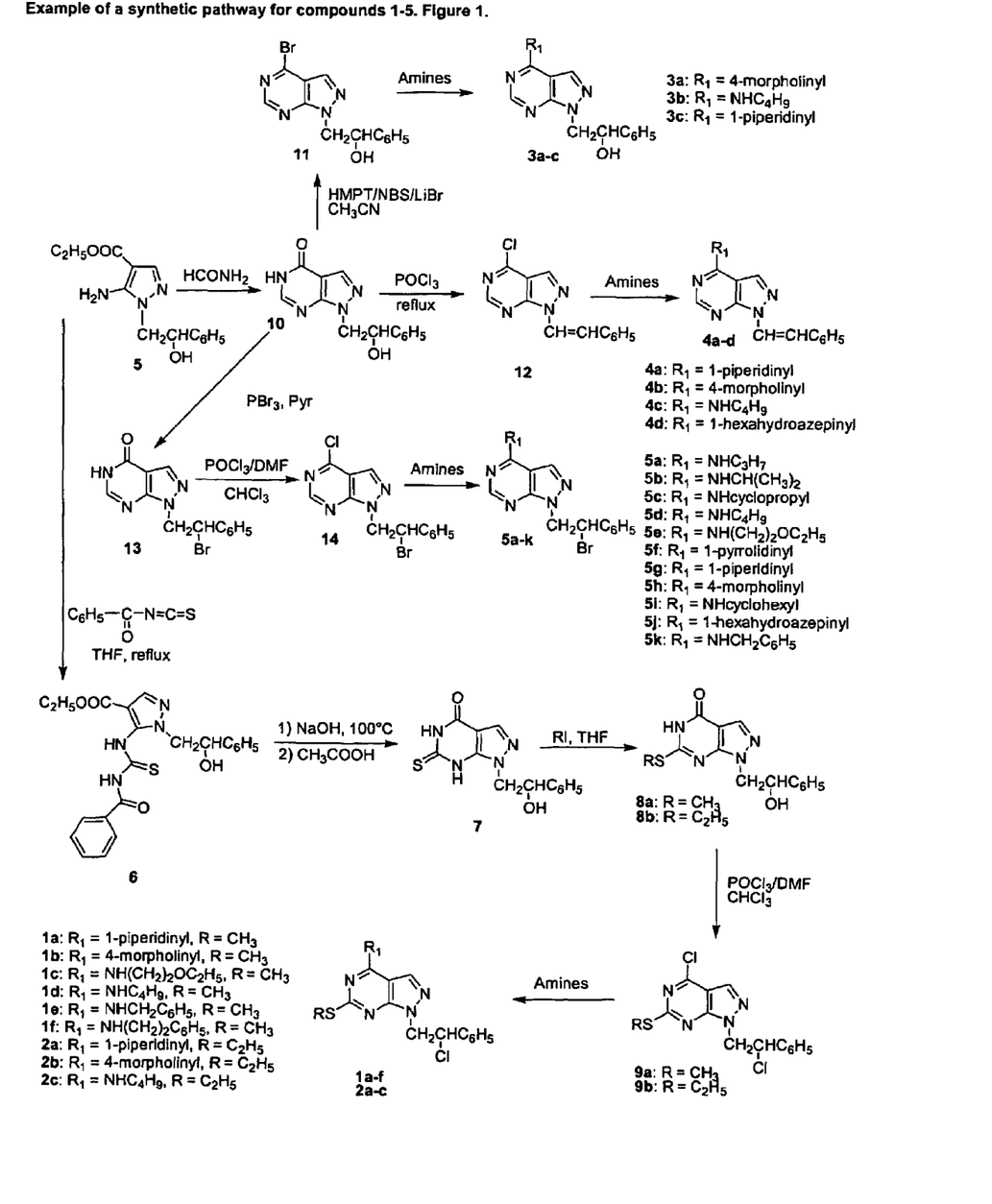
FIG. 1. Synthetic pathway of compounds 1-5.

A scheme is shown in FIG. 1.

Ethyl 5-{[(benzoylamino)carbonothioyl]amino}-1-(2-hydroxy-2-phenylethyl)-1H-pyrazole-4-carboxylate (6)

A suspension of 5 (2.7 g, 10 mmol) and benzoyl isothiocyanate (1.7 g, 11 mmol) in anhydrous tetrahydrofuran (THF) (20 mL) was refluxed for 12 h. The solvent was evaporated under reduced pressure; the oil residue crystallized adding diethyl ether (30 mL) to afford the pure product 6 (4.07 g, 93%) as a white solid; mp 171-172° C. $^1$H NMR: δ 1.29 (t, J=7.0, 3H, $CH_3$), 3.97-4.20 (m, 5H, $2CH_2$+OH, 1H disappears with $D_2O$), 4.58-4.68 (m, 1H, CHO), 7.05-7.98 (m, 10H Ar), 8.02 (s, 1H, H-3), 8.70 (s, 1H, NH, disappears with $D_2O$), 12.05 (s, 1H, NH, disappears with $D_2O$). IR $cm^{-1}$: 3221 (NH), 3190-2940 (OH), 1708 and 1671 (2 CO). Anal. ($C_{22}H_{22}N_4O_4S$) C, H, N, S.

1-(2-Hydroxy-2-phenylethyl)-6-thioxo-1,5,6,7-tetrahydro-4H-pyrazolo[3,4-d]pyrimidin-4-one (7)

A solution of 6 (4.38 g, 10 mmol) in 2 M NaOH (40 mL) was refluxed for 10 min and successively diluted with $H_2O$ (40 mL). The solution was acidified with glacial acetic acid. Standing in a refrigerator for 12 h, a solid crystallized, and was filtered and recrystallized from absolute ethanol to give 7 (2.3 g, 80%) as a white solid; mp 264-265° C. $^1$H NMR: δ 4.15-4.30 and 4.55-4.72 (2m, 2H, $CH_2N$), 4.85-5.00 (m, 1H, CHO), 5.66 (br s, 1H, OH, disappears with $D_2O$), 7.20-7.51 (m, 5H Ar), 8.02 (s, 1H, H-3), 12.20 (s, 1H, NH, disappears with $D_2O$), 13.40 (s, 1H, NH, disappears with $D_2O$). IR $cm^{-1}$: 3362 (NH), 3142-2773 (OH), 1681 (CO). Anal. ($C_{13}H_{12}N_4O_2S$) C, H, N, S.

1-(2-Hydroxy-2-phenylethyl)-6-(methylthio)-1,5-dihydro-4H-pyrazolo[3,4-d]pyrimidin-4-one (8a)

A solution of 7 (2.88 g, 10 mmol) and methyl iodide (7.10 g, 50 mmol) in anhydrous THF (20 mL) was refluxed for 12 h. The solvent and the excess of methyl iodide were removed by distillation under reduced pressure; the oil residue crystallized by adding $CHCl_3$ (10 mL) and was purified by recrystallization with absolute ethanol to give 8a (2.17 g, 72%) as a white solid; mp 208-209° C. $^1$H NMR: δ 2.51 (s, 3H, $CH_3$), 4.27-4.50 (m, 2H, $CH_2N$), 5.04-5.18 (m, 1H, CHO), 5.68 (d, 1H, OH, disappears with $D_2O$), 7.20-7.42 (m, 5H Ar), 7.97 (s, 1H, H-3). IR $cm^{-1}$: 3544 (NH), 3450-3350 (OH), 1678 (CO). Anal. ($C_{14}H_{14}N_4O_2S$) C, H, N, S.

1-(2-Hydroxy-2-phenylethyl)-6-(ethylthio)-1,5-dihydro-4H-pyrazolo[3,4-d]pyrimidin-4-one (8b)

Compound 8b was prepared according to the synthetic sequence described for compound 8a, by using ethyl iodide as alkylating agent. In this case, the crude was purified by column chromatography (Silica Gel, 100 Mesh) using a mixture of $CHCl_3$:MeOH (9:1) as the eluant, to afford the pure product 8b (2.05 g, 65%) as a light yellow solid: mp 199-200° C. $^1$H NMR: δ 1.45 (t, J=7.6, 3H, $CH_3$), 3.22 (q, J=7.4, 2H, $CH_2$), 4.44-4.68 (m, 2H, $CH_2N$), 5.21-5.30 (m, 1H, CHO), 7.26-7.47 (m, 5H Ar), 8.10 (s, 1H, H-3). IR $cm^{-1}$ 3470 (NH), 3450-3340 (OH), 1670 (CO). Anal. ($C_{15}H_{16}N_4O_2S$) C, H, N, S.

4-Chloro-1-(2-chloro-2-phenylethyl)-6-(methylthio)-1H-pyrazolo[3,4-d]pyrimidine (9a)

The Vilsmeier complex, previously prepared from $POCl_3$ (6.13 g, 40 mmol) and anhydrous dimethylformamide (DMF) (2.92 g, 40 mmol) was added to a suspension of 8a (3.02 g, 10 mmol) in $CHCl_3$ (20 mL).

The mixture was refluxed for 4 h. The solution was washed with $H_2O$ (2×20 mL), dried ($MgSO_4$), filtered and concentrated under reduced pressure. The crude oil was purified by column chromatography (Silica gel, 100 Mesh), using a mixture of diethyl ether/petroleum ether (bp 40-60° C.) (1:1) as the eluant, to afford the pure product 9a (2.2 g, 65%) as a white solid, mp 95-96° C. $^1$H NMR: δ 2.62 (s, 3H, $CH_3$), 4.77-5.05 (m, 2H, $CH_2N$), 5.45-5.56 (m, 1H, CHCl), 7.29-7.46 (m, 5H Ar), 8.02 (s, 1H, H-3). Anal. ($C_{14}H_{12}N_4SCl_2$) C, H, N, S.

4-Chloro-1-(2-chloro-2-phenylethyl)-6-(ethylthio)-1H-pyrazolo[3,4-d]pyrimidine (9b)

Compound 9b was prepared according to the synthetic sequence described for compound 9a, starting from 8b, to afford the pure product 9b (2.12 g, 60%) as a white solid, mp 89-90° C.

$^1$H NMR: δ 1.49 (t, J=7.2, 3H, $CH_3$), 3.23 (q, J=7.2, 2H, $CH_2$), 4.75-5.03 (m, 2H, $CH_2N$), 5.43-5.57 (m, 1H, CHCl), 7.28-7.47 (m, 5H Ar), 8.04 (s, 1H, H-3). Anal. ($C_{15}H_{14}N_4SCl_2$) C, H, N, S.

General Procedure for Compounds 1a-f and 2a-c

To a solution of 9a or 9b (10 mmol) in anhydrous toluene (20 mL), the appropriate amine (40 mmol) was added and the reaction mixture was stirred at room temperature for 24 h. The mixture was washed with $H_2O$, the organic phase was dried ($MgSO_4$) and evaporated under reduced pressure; the residue oil crystallized by adding petroleum ether (bp 40-60° C.) (10 mL), to give the products 1a-f and 2a-c.

1a. White solid, yield 60%. $^1$H NMR: δ 1.60-1.82 (m, 6H, $3CH_2$pip), 2.57 (s, 3H, $CH_3$), 3.82-3.98 (m, 4H, $2CH_2$Npip), 4.70-4.97 (m, 2H, $CH_2N$), 5.53-5.64 (m, 1H, CHCl), 7.28-7.49 (m, 5H Ar), 7.81 (s, 1H, H-3). Anal. ($C_{19}H_{22}N_5SCl$) C, H, N, S.

1b. White solid, yield 75%. $^1$H NMR: δ 2.57 (s, 3H, $CH_3$), 3.77-3.87 and 3.89-3.98 (2m, 8H, $4CH_2$morph), 4.71-4.98 (m, 2H, $CH_2N$), 5.51-5.61 (m, 1H, CHCl), 7.26-7.49 (m, 5H Ar), 7.82 (s, 1H, H-3). Anal. ($C_{18}H_{20}N_5OSCl$) C, H, N, S.

1c. White solid, yield 68%. $^1$H NMR: δ 1.21 (t, J=7.0, 3H, $CH_3$), 2.56 (s, 3H, $CH_3S$), 3.53 (q, J=7.0, 2H, O$\underline{CH_2}CH_3$), 3.55-3.85 (m, 4H, $2CH_2$), 4.66-4.97 (m, 2H, $CH_2N$), 5.45-5.60 (m, 1H, CHCl), 5.72 (br s, 1H, NH, disappears with $D_2O$), 7.27-7.44 (m, 5H Ar), 7.77 (s, 1H, H-3). IR $cm^{-1}$: 3441 (NH). Anal. ($C_{18}H_{22}N_5OSCl$) C, H, N, S.

1d. White solid, yield 62%. $^1$H NMR: δ 0.97 (t, J=7.0, 3H, $CH_3$), 1.33-1.84 (m, 4H, $2CH_2$), 2.57 (s, 3H, $CH_3S$), 3.59 (q, J=7.0, 2H, $\underline{CH_2}$NH), 4.70-4.95 (m, 2H, $CH_2N$), 5.49-5.60 (m, 1H, CHCl), 7.23-7.49 (m, 5H Ar), 7.78 (s, 1H, H-3). IR $cm^{-1}$: 3413 (NH). Anal. ($C_{18}H_{22}N_5SCl$) C, H, N, S.

1e. White solid, yield 81%. $^1$H NMR: □ 2.58 (s, 3H, $CH_3$), 4.70-4.94 (m, 4H, $CH_2N$+$\underline{CH_2}$NH), 5.50-5.60 (m, 1H, CHCl), 7.24-7.96 (m, 10H Ar), 7.72 (s, 1H, H-3). IR $cm^{-1}$: 3442 (NH). Anal. ($C_{21}H_{20}N_5SCl$) C, H, N, S.

1f. White solid, yield 76%. $^1$H NMR: δ 2.59 (s, 3H, CH$_3$), 2.98 (q, J=6.0, 2H, CH$_2$Ar), 3.87 (q, J=6.0, 2H, CH$_2$NH), 4.70-4.95 (m, 2H, CH$_2$N), 5.30 (br s, 1H, NH, disappears with D$_2$O), 5.50-5.60 (m, 1H, CHCl), 7.19-7.48 (m, 10H Ar), 7.73 (s, 1H, H-3). IR cm$^{-1}$: 3445 (NH). Anal. (C$_{22}$H$_{22}$N$_5$SCl) C, H, N, S.

2a. White solid, yield 65%. $^1$H NMR: δ 1.46 (t, J=7.4, 3H, CH$_3$), 1.65-1.82 (m, 6H, 3CH$_2$pip), 3.18 (q, J=7.4, 2H, CH$_2$), 3.84-3.96 (m, 4H, 2CH$_2$Npip), 4.70-4.97 (m, 2H, CH$_2$N), 5.53-5.64 (m, 1H, CHCl), 7.28-7.52 (m, 5H Ar), 7.84 (s, 1H, H-3). Anal. (C$_{20}$H$_{24}$N$_5$SCl) C, H, N, S.

2b. White solid, yield 80%. $^1$H NMR: δ 1.46 (t, J=7.4, 3H, CH$_3$), 3.15 (q, J=7.4, 2H, CH$_2$), 3.73-3.88 and 3.90-4.08 (2m, 8H, 4CH$_2$ morph), 4.69-5.00 (m, 2H, CH$_2$N), 5.51-5.62 (m, 1H, CHCl), 7.23-7.56 (m, 5H Ar), 7.82 (s, 1H, H-3). Anal. (C$_{19}$H$_{22}$N$_5$OSCl) C, H, N, S.

2c. White solid, yield 60%. $^1$H NMR: δ 0.95 (t, J=7.6, 3H, CH$_3$but), 1.44 (m, 5H, SCH$_2$CH$_3$+CH$_2$but), 1.60-1.67 (m, 2H, CH$_2$but), 3.18 (q, J=7.6, 2H, CH$_2$S), 3.56 (q, J=6.0, 2H, CH$_2$NH), 4.65-4.90 (m, 2H, CH$_2$N), 5.48-5.59 (m, 1H, CHCl), 7.21-7.49 (m, 5H Ar), 7.78 (s, 1H, H-3). IR cm$^{-1}$: 3400 (NH). Anal. (C$_{19}$H$_{24}$N$_5$SCl) C, H, N, S.

1-(2-Hydroxy-2-phenylethyl)-1,5-dihydro-4H-pyrazolo[3,4-d]pyrimidin-4-one (10)

A suspension of 5 (2.75 g, 10 mmol) in formamide (10 g, 333 mmol) was heated at 190° C. for 8 h and then poured in H$_2$O (300 mL). The crude was filtered and purified by dissolving in 2M NaOH (100 mL), boiling with coal, followed by precipitation with glacial acetic acid. The solid was filtered and recrystallized from absolute ethanol to give 10 (1.79 g, 70%) as a white solid: mp 270-271° C. $^1$H NMR: δ 4.25-4.55 (m, 2H, CH$_2$), 5.05-5.15 (m, 1H, CHO), 5.65 (d, 1H, OH, disappears with D$_2$O), 7.25-7.45 (m, 5H Ar), 8.05 (s, 1H, H-3), 8.10 (s, 1H, H-6), 12.15 (br s, 1H, NH, disappears with D$_2$O). IR cm$^{-1}$: 3400 (NH), 3245-2500 (OH), 1740 (CO). Anal. (C$_{13}$H$_{12}$N$_4$O$_2$) C, H, N.

2-(4-Bromo-1H-pyrazolo[3,4-d]pyrimidin-1-yl)-1-phenylethanol (11)

To a cold (−20° C.) suspension of 10 (2.56 g, 10 mmol) and NBS (7.12 g, 40 mmol) in dry acetonitrile (20 mL), hexamethylphosphorous triamide (HT) (6.53 g, 40 mmol) was added dropwise. After addition, the cold bath was removed and the reaction mixture stirred at room temperature for 0.5 h. LiBr (3.44 g, 40 mmol) was added and the mixture was heated at 70° C. for 5 h. The mixture was evaporated under reduced pressure. The dark oil was purified by column chromatography (Silica Gel, 100 Mesh) using CHCl$_3$ as the eluant, to afford the pure product 11 (1.40 g, 44%) as a white solid: mp 146-147° C. $^1$H NMR: δ 3.46-3.53 (br s, 1H, OH, disappears with D$_2$O), 4.57-4.79 (m, 2H, CH$_2$N), 5.18-5.29 (m, 1H, CHO), 7.30-7.52 (m, 5H Ar), 8.01 (s, 1H, H-3), 8.48 (s, 1H, H-6). IR cm$^{-1}$: 3240-2500 (OH). Anal. (C$_{13}$H$_{11}$N$_4$OBr) C, H, N.

General Procedure for Compounds 3a,b

Compounds 3a,b were prepared according to the synthetic sequence described for compound 1 and 2, starting from product 11.

3a. White solid, yield 75%. $^1$H NMR: δ 3.83-3.94 and 3.95-4.05 (2m, 8H, 4CH$_2$morph), 4.55-4.78 (m, 2H, CH$_2$N), 4.94 (s, 1H, OH, disappears with D$_2$O), 5.20-5.29 (m, 1H, CHO), 7.25-7.51 (m, 5H, Ar), 7.95 (s, 1H, H-3), 8.38 (s, 1H, H-6). IR cm$^{-1}$: 3400-3000 (OH). Anal. (C$_{17}$H$_{19}$N$_5$O$_2$) C, H, N.

3b. White solid, yield 80%. $^1$H NMR: δ 1.01 (t, J=7.6, 3H, CH$_3$), 1.45 (sx, J=7.6, 2H, CH$_2$CH$_3$), 1.62-1.80 (m, 3H, CH$_2$CH$_2$CH$_3$+NH, 1H, disappears with D$_2$O), 3.65 (q, J=7.1, 2H, CH$_2$NH), 4.53-4.77 (m, 2H, CH$_2$N), 5.01 (br s, 1H, OH, disappears with D$_2$O), 5.21-5.32 (m, 1H, CHO), 7.25-7.54 (m, 5H Ar), 7.93 (s, 1H, H-3), 8.37 (s, 1H, H-6). IR cm$^{-1}$: 3400-2900 (OH+NH). Anal. (C$_{17}$H$_{21}$N$_5$O) C, H, N.

4-Chloro-1-(2-phenylvinyl)-1H-pyrazolo[3,4-d]pyrimidine (12)

POCl$_3$ (14 g, 91 mmol) was added to 10 (2.56 g, 10 mmol) and the mixture was refluxed for 12 h and then cooled to room temperature.

The excess of POCl$_3$ was removed by distillation under reduced pressure. H$_2$O (20 mL) was carefully added to the residue and the suspension was extracted with CHCl$_3$ (3×20 mL). The organic solution was washed with H$_2$O (10 mL), dried (MgSO$_4$), filtered and concentrated under reduced pressure. The crude brown oil was purified by column chromatography (Florisil® 100-200 Mesh), using CHCl$_3$ as the eluant to afford the pure product 12 (1.66 g, 65%) as a white solid: mp 139-140° C. $^1$H NMR: δ 7.25-7.61 m, 6H, 5H Ar+CH=), 8.04 (d, J$_{trans}$=14.6, 1H, CH=), 8.29 (s, 1H, H-3), 8.85 (s, 1H, H-6). IR cm$^{-1}$ 1658 (C=C). Anal. (C$_{13}$H$_9$N$_4$Cl) C, H, N.

General Procedure for Compounds 4 a-d

Compounds 4 a-d were prepared according to the synthetic sequence described for compounds 1, 2, and 3 starting from product 12.

4a. White solid, yield 80%. $^1$H NMR: δ 1.68-1.87 (m, 6H, 3CH$_2$), 3.89-4.07 (m, 4H, 2CH$_2$N), 7.20-7.60 (m, 6H, 5H Ar+CH=), 8.08 (s, 1H, H-3), 8.09 (d, J$_{trans}$=14.4, 1H, CH=), 8.42 (s, 1H, H-6). IR cm$^{-1}$ 1655 (C=C). Anal. (C$_{18}$H$_{19}$N$_5$) C, H, N.

4b. White solid, yield 85%. $^1$H NMR: δ 3.85-3.93 and 3.96-4.05 (2m, 8H, 4CH$_2$morph), 7.20-7.55 (m, 6H, 5H Ar+CH=), 8.06 (s, 1H, H-3), 8.07 (d, J$_{trans}$=14.3, 1H, CH=), 8.44 (s, 1H, H-6). IR cm$^{-1}$ 1655 (C=C). Anal. (C$_{17}$H$_{17}$N$_5$O) C, H, N.

4c. White solid, yield 64%. $^1$H NMR: δ 0.99 (t, J=7.2, 3H, CH$_3$), 1.38-1.58 (sx, J=7.2, 2H, CH$_2$CH$_3$), 1.62-1.80 (m, J=7.2, 2H, CH$_2$), 3.65 (q, J=7.2, 2H, CH$_2$N), 5.35-5.60 (br s, 1H, NH, disappears with D$_2$O), 7.20-7.58 (m, 6H, 5H Ar+CH=), 8.02 (s, 1H, H-3), 8.04 (d, J$_{trans}$=14.4, 1H, CH=), 8.42 (s, 1H, H-6). IR cm$^{-1}$ 1650 (C=C). Anal. (C$_{17}$H$_{19}$N$_5$) C, H, N.

4d. White solid, yield 72%. $^1$H NMR: δ 1.53-1.73 (m, 4H, 2CH$_2$), 1.82-2.08 (m, 4H, 2CH$_2$), 3.80-4.08 (m, 4H, 2CH$_2$N), 7.20-7.62 (m, 6H, 5H Ar+CH=), 8.05 (s, 1H, H-3), 8.07 (d, J$_{trans}$=14.4, 1H, CH=), 8.43 (s, 1H, H-6). IR cm$^{-1}$ 1655 (C=C). Anal. (C$_{19}$H$_{21}$N$_5$) C, H, N.

1-(2-Bromo-2-phenylethyl)-1,5-dihydro-4H-pyrazolo[3,4-d]pyrimidin-4-one (13)

To a suspension of 10 (2.56 g, 10 mmol), in anhydrous DMF (20 mL), cooled at 0° C., was added dropwise a solution of phoshorous tribromide (3.27 g, 12,1 mmol), pyridine (0.5 mL) and toluene (5 mL) previously prepared. The mixture was stirred at r.t. for 3 days. The solvent was removed under reduced pressure, the residue was poured in water and ice (200 mL). The white solid was filtered and crystallized from absolute ethanol, to give pure product 3 (1.91 g; 60%): mp 230-231° C. $^1$H NMR: δ 4.80-4.97 and 5.01-5.19 (2m, 2H, CH$_2$N), 5.68-5.72 (m, 1H, CHBr), 7.30-7.65 (m, 5H Ar), 7.97 (s, 1H, H-3), 8.13 (s, 1H, H-6), 12.25 (br s, 1H, NH, disappears with D$_2$O). IR (KBr) cm$^{-1}$ 3440 (NH), 1665 (C=O).

1-(2-Bromo-2-phenylethyl)-4-chloro-1H-pyrazolo[3,4-d]pyrimidine (14)

The Vilsmeier complex, previously prepared from POCl$_3$ (2.45 g, 16 mmol) and anhydrous dimethylformamide (DMF) (1.16 g, 16 mmol) was added to a suspension of 3 (0.5 g, 1.56 mmol) in CHCl$_3$ (10 mL).

The mixture was refluxed for 12 h. The solution was washed with H$_2$O (2×20 mL), dried (MgSO$_4$), filtered and concentrated under reduced pressure. The crude oil was purified by column chromatography (Florisil®, 100 Mesh), using CH$_2$Cl$_2$ as eluant, to afford the pure product 4 (0.41 g, 78%) as a white solid, mp 114-115° C. $^1$H NMR: δ 4.95-5.38 (m, 2H, CH$_2$N), 5.58-5.78 (m, 1H, CHCl), 7.25-7.70 (m, 5H Ar), 8.17 (s, 1H, H-3), 8.77 (s, 1H, H-6).

General procedure for 1-(2-bromo-2-phenylethyl)-1H-pyrazolo[3,4-d]pyrimidines 4-amino substituted 5a-k To a solution of 14 (0.3 g, 1 mmol) in anhydrous toluene (5 mL), the proper amine (4 mmol) was added, and the reaction mixture was stirred at room temperature for 36 h. After it was extracted with H$_2$O (10 mL), the organic phase was dried (MgSO$_4$), filtered and concentrated under reduced pressure; the oil residue crystallized by adding absolute ethanol (10 mL) to give products 5a-k.

5a. White solid, mp 136-137° C., yield 60%. $^1$H NMR δ 1.06 (t, J=7.6, 3H, CH$_3$), 1.75 (q, J=7.6, 2H, CH$_2$CH$_3$), 3.60 (q, J=7.4, 2H, NHCH$_2$), 3.90 (br s, 1H, NH disappears with D$_2$O), 4.85-5.20 (m, 2H, CH$_2$N), 5.60-5.72 (m, 1H, CHBr), 7.25-7.54 (m, 5H Ar), 7.90 (s, 1H, H-3), 8.17 (s, 1H, H-6). IR (KBr) cm$^{-1}$ 3214 (NH).

5b. White solid, mp 150-141° C., yield 65%. $^1$H NMR δ 1.36 (d, J=6.4, 6H, 2CH$_3$), 4.20 (m, 1H, NHCH), 4.84-5.20 (m, 2H, CH$_2$N), 5.60-5.70 (m, 1H, CHBr), 7.24-7.56 (m, 5H Ar), 7.88 (s, 1H, H-3), 8.39 (s, 1H, H-6). IR (KBr) cm$^{-1}$ 3219 (NH).

5c. White solid, mp 162-163° C., yield 70%. $^1$H NMR δ 0.68-0.88 (m, 2H, CH$_2$), 0.94-1.10 (m, 2H, CH$_2$), 2.88-3.03 (m, 1H, NH—CH), 4.85-5.24 (m, 2H, CH$_2$N), 5.56-5.71 (m, 1H, CHBr), 7.08 (br s, 1H, NH, disappears with D$_2$O), 7.22-7.58 (m, 5H Ar), 8.18 (s, 1H, H-3), 8.34 (s, 1H, H-6). IR (KBr) cm$^{-1}$ 3214 (NH).

5d. White solid, mp 95-96° C., yield 70%. $^1$H NMR δ 0.99 (t, J=7.2, 3H, CH$_3$), 1.49 (sext, J=7.4, 2H, CH$_2$CH$_3$), 1.71 (quint, J=7.2, 2H, CH$_2$CH$_2$CH$_3$), 3.61 (q, J=7.2, 2H, NH CH$_2$), 4.83-5.18 (m, 2H, CH$_2$N), 5.38 (br s, 1H, NH, disappears with D$_2$O), 5.60-5.70 (m, 1H, CHBr), 7.28-7.58 (m, 5H Ar), 7.90 (s, 1H, H-3), 8.37 (s, 1H, H-6). IR (KBr) cm$^{-1}$ 3227 (NH).

5e. White solid, mp 109-110° C., yield 60%. $^1$H NMR δ 1.25 (t, J=7.0, 3H, CH$_3$), 3.57 (q, J=7.0, 2H, OCH$_2$CH$_3$), 3.69 (q, J=5.0, 2H, NHCH$_2$), 3.82 (t, J=5.0, 2H, OCH$_2$), 4.83-5.20 (m, 2H, CH$_2$N), 5.40-5.60 (m, 1H, CHBr), 5.80 (br s, 1H, NH, disappears with D$_2$O), 7.23-7.52 (m, 5H Ar), 7.90 (s, 1H, H-3), 8.40 (s, 1H, H-6). IR (KBr) cm$^{-1}$ 3120 (NH).

5f. White solid, mp 127-128° C., yield 65%. $^1$H NMR δ 1.89-2.16 (m, 4H, 2CH$_2$ pyrr), 3.79 (t, J=6.8, 4H, 2CH$_2$N pyrr), 4.84-5.18 (m, 2H, CH$_2$N), 5.61-5.70 (m, 1H, CHBr), 7.25-7.56 (m, 5H Ar), 7.91 (s, 1H, H-3), 8.38 (s, 1H, H-6).

5g. White solid, mp 144-145° C., yield 68%. $^1$H NMR δ 1.64-1.84 (m, 6H, 3CH$_2$ pip), 3.86-4.01 (m, 4H, 2CH$_2$—N pip), 4.84-5.19 (m, 2H, CH$_2$N), 5.63-5.73 (m, 1H, CHBr), 7.25-7.54 (m, 5H Ar), 7.94 (s, 1H, H-3), 8.37 (s, 1H, H-6)

5h. White solid, mp 111-112° C., yield 67%. $^1$H NMR δ 3.87 and 3.97 (2m, 8H, 4CH$_2$ morph), 4.85-5.22 (m, 2H, CH$_2$N), 5.63-5.73 (m, 1H, CHBr), 7.28-7.55 (m, 5H Ar), 7.95 (s, 1H, H-3), 8.40 (s, 1H, H-6)

5i. White solid, mp 154-155° C., yield 70%. $^1$H NMR δ 1.20-2.20 (m, 10H, 5CH$_2$), 3.38-4.18 (m, 1H, CH), 4.71-5.19 (m, 2H, CH$_2$N), 5.58-5.70 (m, 1H, CHBr), 7.23-7.57 (m, 5H Ar), 7.85 (s, 1H, H-3), 8.36 (s, 1H, H-6). IR (KBr) cm$^{-1}$ 3251 (NH).

5j. White solid, mp 124-125° C., yield 64%. $^1$H NMR δ 1.53-1.68 (m, 4H, 2CH$_2$ hexamet), 1.82-2.02 (m, 4H, 2CH$_2$ hexamet), 3.77-4.03 (m, 4H, 2CH$_2$N hexamet), 4.83-5.19 (m, 2H, CH$_2$N), 5.64-5.71 (m, 1H, CHBr), 7.24-7.57 (m, 5H Ar), 7.88 (s, 1H, H-3), 8.38 (s, 1H, H-6)

5k. White solid, mp 157-158° C., yield 80%. $^1$H NMR δ 4.84 (d, 2H, CH$_2$Ar), 4.86-5.19 (m, 2H, CH$_2$N), 5.60-5.71 (m, 1H, CHBr), 7.26-7.54 (m, 10H Ar), 7.85 (s, 1H, H-3), 8.43 (s, 1H, H-3). IR (KBr) cm$^{-1}$ 3214 (NH).

EXAMPLE 2

Inhibitory Activity Toward Different Tumor Cell Lines

The aim of these experiments was the evaluation of the antiproliferative activity of the invented compounds. In particular, such compounds were evaluated for their ability to inhibit tumor cell proliferation. To demonstrate the possible applications of these compounds toward different neoplastic targets, four different cell lines were chosen. 1) A431 human epidermoid carcinoma cells,[10] known to overexpress both epithelial growth factor receptor (EGFR) and Src 2) 8701-BC breast cancer cells,[11] established from a primary ductal infiltrating carcinoma, that is, before the clonal selection of the metastatic process. This cell line maintains a number of properties in culture that are typical of the mammary tumor cells and is known to overexpress Src tyrosine kinase (TK).[12] 3) K-562 cell line was established from the pleural effusion of a 53-year-old female with chronic myelogenous leukemia in terminal blast crise. K-562 blasts are multipotential, hematopoietic malignant cells that are able to spontaneously differentiate. 4) The MEG-01 cell line was derived in 1983 from bone marrow cells taken from a patient in megakaryoblastic crisis of chronic myeloid leukemia.

K562 and MEG-01 cells are positive for Bcr-Abl, a couple of kinases expressed in the myeloid cells and belonging to the Lyn and Hck members, respectively, of the Src tyrosine kinase family.

Material and Methods

Compounds were dissolved in 0,1 M DMSO and further diluted to the appropriate concentration in the adequate cell culture medium. PP2, (1-(t-butyl)-3-(4-methylphenyl)-4-aminopyrazolo[3,4-d]pyrimidine, was chosen as the reference compound for its potency and selective effects toward the Src family of tyrosine kinases.[13-18]

Cell Proliferation Assay

A431 (2×10$^4$ cells/mL) were incubated in 100 mL DMEM culture medium (BioWhittaker, Vallensbaek, DK). Differently, 8701-BC (2×10$^4$ cells/mL) were incubated in 100 µL RPMI 1640 culture medium (BioWhittaker, Vallensbaek, DK). Both cell lines were supplemented with 10% foetal calf serum (FCS; BioWhittaker, Vallensbaek, DK) and antibiotics (100 U/mL penicillin and 100 μg/mL streptomycin), at 37° C. in 5% $CO_2$ for 8 hours, to allow adhesion. After adhesion, the medium was replaced with 100 μL medium supplemented with 0.5% FCS. After an overnight incubation, the medium was replaced and 100 μL DMEM with 10% FCS along with different concentrations (0-100 μM) of the studied compounds were added to cell cultures.

Following 72 hours, cells were treated with 10 μL of the 3-(4,5-dimethylthiazol-2-yl)-5-(3-carboxymethoxyphenyl)-2-(4-sulfonyl)-2H-tetrazolium (MTT) solution (5 mg/mL). Four hours later, 100 μL of propan-2-ol in a 0.04 M HCl solution were added to dissolve the formazan product. The microplates were read using an ELISA plate reader at 570 nm with a reference wavelength of 630 nm.

MEG-01 and K562 ($2 \times 10^4$ cells/mL) were incubated in 100 μL RPMI 1640 culture medium (BioWhittaker, Vallensbaek, DK), supplemented with 10% foetal calf serum (FCS; BioWhittaker, Vallensbaek, DK) and antibiotics (100 U/mL penicillin and 100 μg/mL streptomycin), at 37° C. in 5% $CO_2$. After an overnight incubation with 100 μL medium supplemented with 0.5% FCS, the medium was replaced and 100 μL RPMI 1640 with 10% FCS along with different concentrations (0-100 μM) of the studied compounds, were added to cell cultures.

Phospho-Src Inhibition by Compounds Toward A431 and 8701-BC Cells

Immunoblot analysis was performed using phospho-specific antibodies to Src (Tyr416). Filters were additionally reprobed with specific non-phospho anti-Src antibodies after stripping.

8701-BC immunoblot analyses. Cells were treated as reported above but the cells were challenged with the compounds for 3 h, and then treated with 100 nM EGF (Cell Signaling Technology, MA, U.S.A.). Five minutes later, cells were harvested and lysed in an appropriate buffer containing 1% Triton X-100. Proteins were quantitated by the BCA method (Pierce Rockford, U.S.A.). Equal amounts of total cellular protein were resolved by SDS-polyacrylamide gel electrophoresis, transferred to nitrocellulose filters and subjected to immunoblot using phospho-specific antibodies against Src (Y416) and non pospho-specific Src as control (Cell Signaling Technology, MA, U.S.A.).

Figure 4:
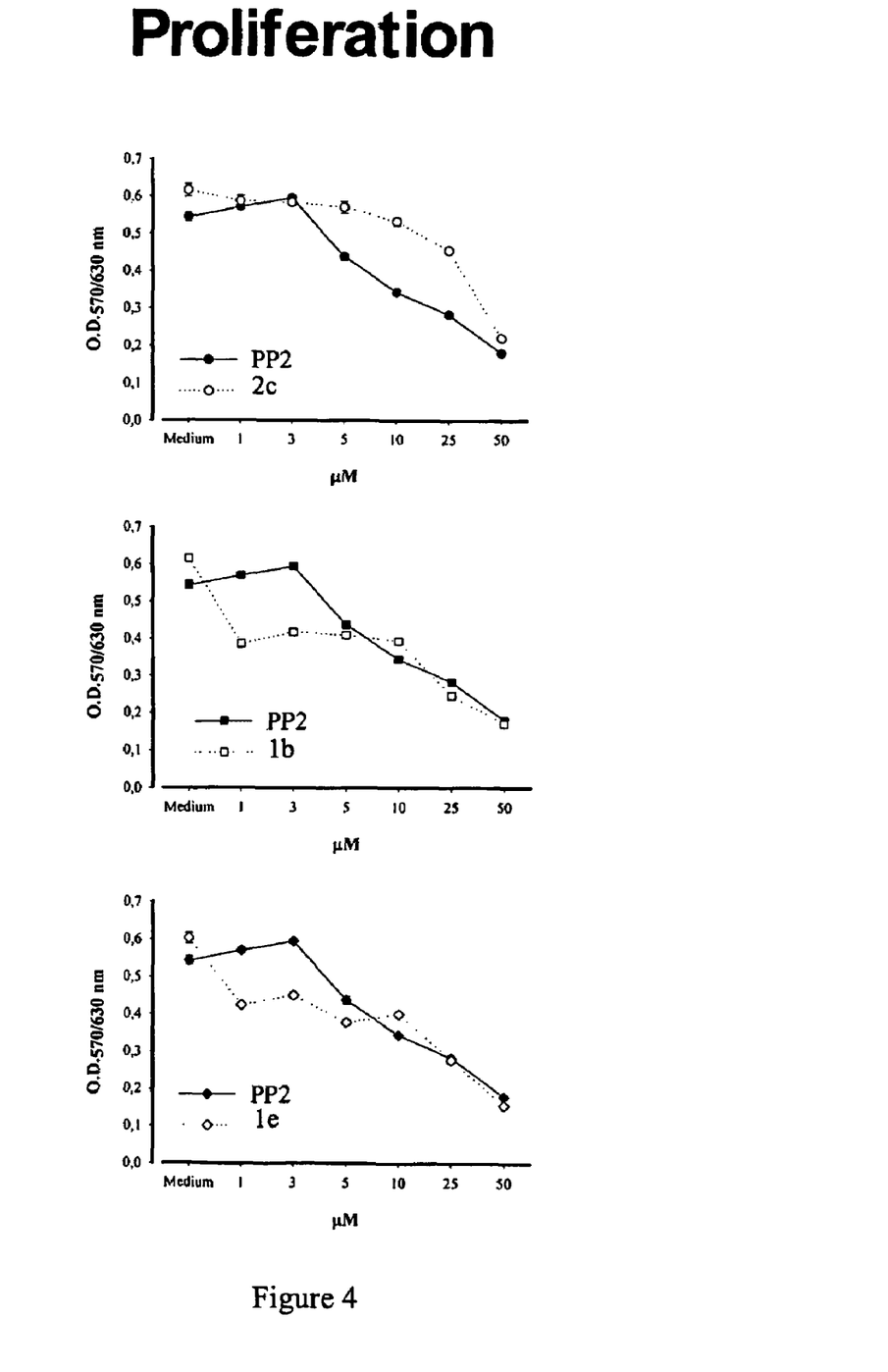
FIG. 4. Inhibitory effects of compounds 2c, 1b and 1e on the growth of A431 cells measured by the MTT assay.[21] Values are means±SEM of three independent experiments performed in duplicates.

A431 immunoblot analyses. Phosphorylation of Src Tyr416 is a crucial step in the mechanism of the enzyme activation.[19] A431 cells have been well characterized in respect to EGF-dependent signal transduction. In more details, these cells express high levels of EGF receptor on their surface and proliferate in response to autocrine secretion of transforming growth factor-α,[20] but they also require phosphorylation of Src to proliferate. To determine whether these pyrazolo-pyrimidine compounds were able to inhibit the phosphorylation of Src Tyr416, we used a phosphospecific anti-Src (Tyr416) antibody (Cell Signaling Technology, MA, U.S.A.). PP2, used as a reference compound, has been identified as a Src-selective tyrosine kinase inhibitor and has been used extensively to investigate signalling pathways involving Src kinases, including events downstream of the stem cell factor (SCF) receptor c-Kit.[16] As a result, we found that compounds 1b, 1e, and 2c were able to inhibit Src phosphorylation with almost the same efficacy of PP2 (FIG. 4, Table 3).

Cytotoxicity

The cytotoxic effect of compound was evaluated by trypan blue exclusion. Cells were stimulated for 1 h at 37° C. with the increasing concentrations (10 nM-10 μM) of the test compound in 1% FCS medium. Cells were then stained with 0.4% trypan blue in phosphate buffer saline (PBS) for 5 min. The number of dead and living cells was counted at the microscope in a blind manner. The percentage of dead cells over the total number of cells was calculated. All the compounds reported in Table 1 showed no citotoxicity (at the tested concentrations) toward the cell lines reported.

Results

Results of the antiproliferative activity of the compounds toward A431 and 8701-BC cells are reported in Table 1 in comparison with the activity of PP2 chosen as the reference compound.

TABLE 1

Activity data (expressed as $IC_{50}$ values) of some pyrazolo-pyrimidines toward 8701-BC and A431 cells.

| | | | | | | | $IC_{50}$ (μM) | |
| --- | --- | --- | --- | --- | --- | --- | --- | --- |
| Compd. | R | $R_1$ | $R_2$ | $R_3$ | $R_4$ | $R_5$ | 8701-BC$^a$ | A431$^b$ |
| 1a | $SCH_3$ | 1-piperidinyl | H | H | —$CH_2CH(R_5)$—Ph | Cl | 67.5 ± 1.2 | 37.6 ± 0.8 |
| 1b | $SCH_3$ | 4-morpholinyl | H | H | —$CH_2CH(R_5)$—Ph | Cl | 64.2 ± 1.8 | 26.9 ± 0.4 |

TABLE 1-continued

Activity data (expressed as IC$_{50}$ values) of some pyrazolo-pyrimidines toward 8701-BC and A431 cells.

| Compd. | R | R$_1$ | R$_2$ | R$_3$ | R$_4$ | R$_5$ | IC$_{50}$ (μM) 8701-BC[a] | A431[b] |
|---|---|---|---|---|---|---|---|---|
| 1c | SCH$_3$ | NH(CH$_2$)$_2$OC$_2$H$_5$ | H | H | —CH$_2$CH(R$_5$)—C$_6$H$_5$ | Cl | 59.8 ± 3.1 | 32.4 ± 0.6 |
| 1d | SCH$_3$ | NHC$_4$H$_9$ | H | H | —CH$_2$CH(R$_5$)—C$_6$H$_5$ | Cl | 63.8 ± 2.1 | 27.4 ± 0.5 |
| 1e | SCH$_3$ | NHCH$_2$C$_6$H$_5$ | H | H | —CH$_2$CH(R$_5$)—C$_6$H$_5$ | Cl | 53.2 ± 1.2 | 24.6 ± 0.7 |
| 1f | SCH$_3$ | NH(CH$_2$)$_2$C$_6$H$_5$ | H | H | —CH$_2$CH(R$_5$)—C$_6$H$_5$ | Cl | 31.2 ± 0.5 | 27.1 ± 0.2 |
| 1g | SCH$_3$ | NHC$_3$H$_7$ | H | H | —CH$_2$CH(R$_5$)—C$_6$H$_5$ | Cl | 64.1 ± 0.5 | 32.1 ± 0.5 |
| 1h | SCH$_3$ | NH(C$_2$H$_5$)$_2$ | H | H | —CH$_2$CH(R$_5$)—C$_6$H$_5$ | Cl | 86.9 ± 1.2 | 70.2 ± 1.4 |
| 1i | SCH$_3$ | 1-pyrrolidinyl | H | H | —CH$_2$CH(R$_5$)—C$_6$H$_5$ | Cl | 56.3 ± 2.0 | 32.3 ± 0.8 |
| 1j | SCH$_3$ | 1-hexahydroazepinyl | H | H | —CH$_2$CH(R$_5$)—C$_6$H$_5$ | Cl | 54.4 ± 0.8 | NA |
| 1k | SCH$_3$ | NHcyclohexyl | H | H | —CH$_2$CH(R$_5$)—C$_6$H$_5$ | Cl | 35.3 ± 0.5 | 43.8 ± 0.7 |
| 2a | SC$_2$H$_5$ | 1-piperidinyl | H | H | —CH$_2$CH(R$_5$)—C$_6$H$_5$ | Cl | NA | NA |
| 2b | SC$_2$H$_5$ | 4-morpholinyl | H | H | —CH$_2$CH(R$_5$)—C$_6$H$_5$ | Cl | 79.8 ± 3.0 | 42.3 ± 0.7 |

TABLE 1-continued

Activity data (expressed as IC$_{50}$ values) of some pyrazolo-pyrimidines toward 8701-BC and A431 cells.

| Compd. | R | R$_1$ | R$_2$ | R$_3$ | R$_4$ | R$_5$ | IC$_{50}$ (μM) 8701-BC[a] | A431[b] |
|---|---|---|---|---|---|---|---|---|
| 2c | SC$_2$H$_5$ | NHC$_4$H$_9$ | H | H | —CH$_2$CH(R$_5$)—C$_6$H$_5$ | Cl | 38.8 ± 0.5 | 40.2 ± 0.4 |
| 2d | SC$_2$H$_5$ | NHC$_3$H$_7$ | H | H | —CH$_2$CH(R$_5$)—C$_6$H$_5$ | Cl | 28.6 ± 1.6 | 79.4 ± 1.8 |
| 2e | SC$_2$H$_5$ | 1-pyrrolidinyl | H | H | —CH$_2$CH(R$_5$)—C$_6$H$_5$ | Cl | 72.1 ± 1.7 | 89.3 ± 1.7 |
| 2f | SC$_2$H$_5$ | NHCH$_2$C$_6$H$_5$ | H | H | —CH$_2$CH(R$_5$)—C$_6$H$_5$ | Cl | 42.8 ± 0.8 | NA |
| 3a | H | 4-morpholinyl | H | H | —CH$_2$CH(R$_5$)—C$_6$H$_5$ | OH | NA | 86.9 ± 2.1 |
| 3b | H | NHC$_4$H$_9$ | H | H | —CH$_2$CH(R$_5$)—C$_6$H$_5$ | OH | NA | 83.2 ± 1.8 |
| 3c | H | 1-piperidinyl | H | H | —CH$_2$CH(R$_5$)—C$_6$H$_5$ | OH | NA | 13.4 ± 0.2 |
| 3d | H | NHC$_3$H$_7$ | H | H | —CH$_2$CH(R$_5$)—C$_6$H$_5$ | OH | NA | 91.2 ± 1.4 |
| 3e | H | NHCH$_2$C$_6$H$_5$ | H | H | —CH$_2$CH(R$_5$)—C$_6$H$_5$ | OH | NA | 12.7 ± 0.7 |
| 3f | H | NHCH$_2$CH$_2$C$_6$H$_5$ | H | H | —CH$_2$CH(R$_5$)—C$_6$H$_5$ | OH | 45.6 ± 0.5 | 80.1 ± 2.5 |

TABLE 1-continued

Activity data (expressed as IC$_{50}$ values) of some pyrazolo-pyrimidines toward 8701-BC and A431 cells.

| Compd. | R | R$_1$ | R$_2$ | R$_3$ | R$_4$ | R$_5$ | IC$_{50}$ (μM) 8701-BC[a] | A431[b] |
|---|---|---|---|---|---|---|---|---|
| 3g | H | NHCH$_2$(p-F)C$_6$H$_4$ | H | H | —CH$_2$CH(R$_5$)—C$_6$H$_5$ | OH | 54.4 ± 1.5 | 95.7 ± 2.3 |
| 4a | H | 1-piperidinyl | H | H | styryl | | NA | 69.3 ± 1.2 |
| 4b | H | 4-morpholinyl | H | H | styryl | | 58.8 ± 0.7 | 59.2 ± 1.0 |
| 4c | H | NHC$_4$H$_9$ | H | H | styryl | | 80.5 ± 6.8 | 91.5 ± 2.0 |
| 4d | H | 1-hexahydroazepinyl | H | H | styryl | | 93.7 ± 0.6 | 43.6 ± 1.3 |
| 4e | H | NHC$_3$H$_7$ | H | H | styryl | | 57.2 ± 0.8 | 61.2 ± 1.0 |
| 4f | H | NH(CH$_2$)$_2$OC$_2$H$_5$ | H | H | styryl | | 43.4 ± 0.4 | NA |
| 4g | H | 1-pyrrolidinyl | H | H | styryl | | 50.4 ± 0.1 | 63.1 ± 1.0 |
| 4h | H | NHcyclohexyl | H | H | styryl | | 50.5 ± 1.3 | NA |
| 4i | H | NHCH$_2$C$_6$H$_5$ | H | H | styryl | | 65.0 ± 0.3 | 11.7 ± 0.1 |
| 4j | H | NHCH$_2$CH$_2$C$_6$H$_5$ | H | H | styryl | | 64.7 ± 0.6 | 15.0 ± 1.2 |
| 4k | SC$_2$H$_5$ | 4-morpholinyl | H | H | styryl | | | 49.8 ± 0.8 |
| 4l | SCH$_3$ | NHCH$_2$C$_6$H$_5$ | H | H | styryl | | | 39.8 ± 0.6 |
| 4m | SCH$_3$ | 1-piperidinyl | H | H | styryl | | | 54.1 ± 0.7 |
| 4n | SCH$_3$ | 4-morpholinyl | H | H | styryl | | | 35.7 ± 0.6 |
| 5d | H | NHC$_4$H$_9$ | H | H | —CH$_2$CH(R$_5$)—C$_6$H$_5$ | Br | | 33.6 ± 1.2 |
| 5i | H | NHcyclohexyl | H | H | —CH$_2$CH(R$_5$)—C$_6$H$_5$ | Br | | 28.2 ± 0.4 |
| AG1478 | | | | | | | | 20.2 ± 0.4 |
| PP2 | | | | | | | 61.8 ± 4.4 | 31.9 ± 0.7 |

[a] IC$_{50}$ values were determined on exponentially growing 8701-BC cells incubated with each of the compounds (0-100 μM) for 72 hours using the MTT assay.[21] The IC$_{50}$ values are means ± SEM of three independent experiments performed in duplicates.

NA = not active at 100 μM concentration. IC$_{50}$ values are means ± SEM of series separate assays, each performed in quadruplicate.

[b] To test our system, we have used the well known antiproliferative agent AG1478. As a result, the IC$_{50}$ of such compound toward A431 cells (20 μM), was comparable with that reported in the literature.[22] However, since the studied compounds were found to inhibit Src phosphorylation, we discussed their structure-activity relationships in comparison to the activity of PP2, known as a very potent and selective inhibitor of Src phosphorylation. IC$_{50}$ values are means ± SEM of series separate assays, each performed in quadruplicate.

Figure 2:
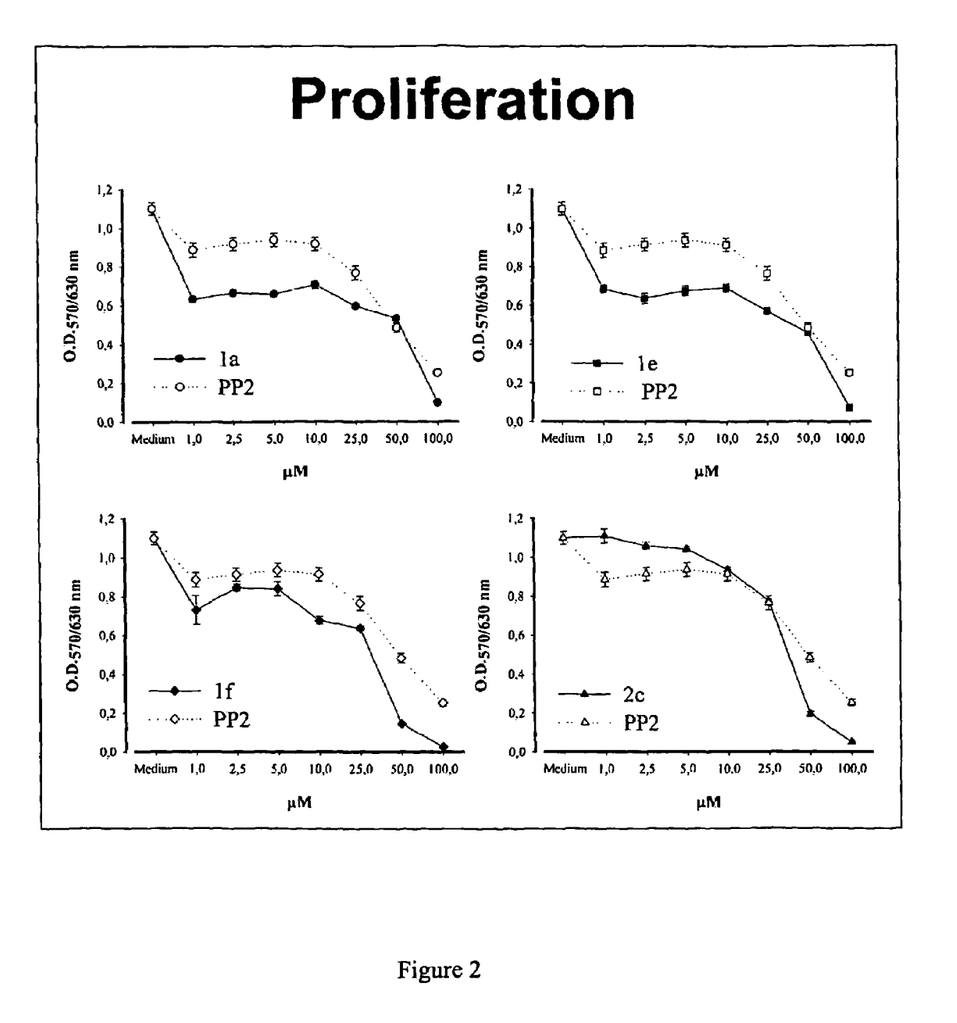
FIG. 2. Inhibitory effects of compounds 1a, 1e, 1f, and 2c on the growth of 8701-BC cells measured by the MTT assay.[21] Values are means±SEM of three independent experiments performed in duplicates.

To investigate the antiproliferative activity of these compounds, their inhibitory effect toward the phosphorylation of Src (Tyr416), was tested on 8701-BC cells treated with 100 nM (epithelial growth factor) EGF. Many of the newly synthesized compounds (namely, 1b-g, 1i-k, 2c, d, f, 3f, g, and 4b, e-h, corresponding to about 50% of the total number of compounds) were characterized by an antiproliferative activity toward 8701-BC cells ranging between 31.2 (1f) and 64.2 μM (1b), comparable to or better than that of PP2 (61.8 μM, FIG. 2, Table 1).

TABLE 2

Inhibitory effects of compounds 1a, 1e, 1f, and 2c on phospho-Src after EGF stimulation of 8701-BC cells measured by immuno blot. Value are expressed as area units of the corresponding gels reported in FIG. 2.

| | Control | Control + EGF[a] | PP2[a] | 1a[a] | 1e[a] | 1f[a] | 2c[a] |
|---|---|---|---|---|---|---|---|
| Non-phospho-Src | 52 | 121 | 191 | 125 | 98 | 168 | 80 |
| Phospho-Src (Tyr416) | 12 | 68 | 43 | 22 | 17 | 15 | 28 |
| Phospho-Src/Non-phospho-Src ratio (%) | 23 | 56 | 23 | 18 | 17 | 9 | 35 |

[a] 8701-BC cells treated for 15 min with 100 nM EGF

Figure 3:
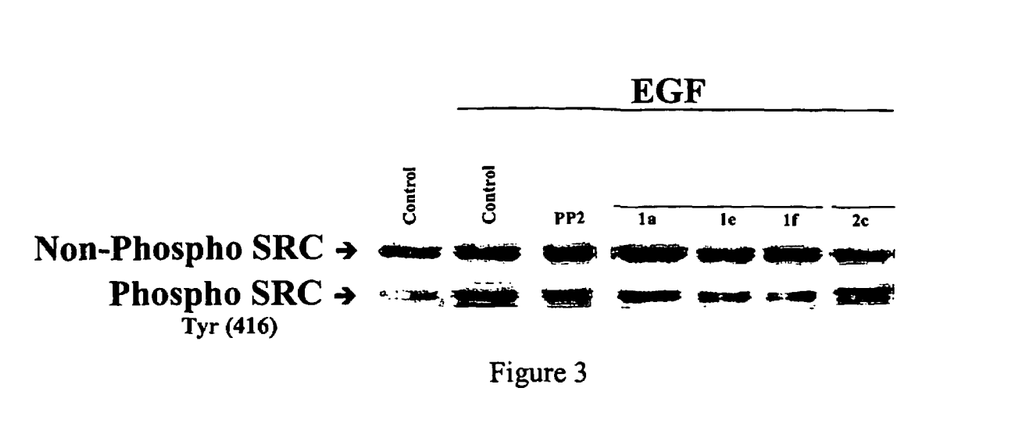
FIG. 3. Phospho-Src inhibition by compounds 1a, 1e, 1f, and 2c toward 8701-BC cells, with respect to the reference compound PP2. Immunoblot analysis was performed using phospho-specific antibodies to Src (Tyr416). Filters were additionally reprobed with specific non-phospho anti-Src antibodies after stripping. Lane 1: cell control; lane 2: cells treated for 15 min with EGF (100 nM); lane 3-7: cells challenged for 3 h in the presence of 10 μM of the specified compound and then treated for 15 min with EGF (100 nM). Results are representative of three independent experiments.

Moreover, since one of the possible targets (but not the only one) was represented by the inhibition of the phosphorylation of the Src enzyme, we tested Phospho-Src inhibition by compounds in both A431 and 8701-BC cells. Immunoblot analysis, performed using phospho-specific antibodies to Src (Tyr416), clearly showed an inhibition of the Src activation-phosphorylation of 8701-BC cells exposed to the studied compounds, with respect to the control. In particular, compounds 1a, 1e and 1f were found to inhibit Src phosphorylation better than the reference compound PP2 (FIG. 3). Differently, although compound 2c retained an appreciable inhibitory activity, it was found less potent than PP2. The occurrence, at the same time, of a reduction of Src phosphorylation and an inhibition of cell proliferation, led us to assume that our compounds were able to inhibit proliferation through inhibition of Src phosphorylation, since the latter mediates a cascade leading to the stimulation of cell proliferation and mobility.

Regarding the antiproliferative activity toward A431 cells, eleven compounds (namely, 1b-g, 1i, 3c,e, and 4i,j, Table 1) were found to have IC$_{50}$ activity values comparable to or better than that of the reference compound PP2 (32 μM). FIG. 4 and Table 3 show the antiproliferative activity of the most interesting compounds (1b, 1e, and 2c) with respect to PP2.

TABLE 3

Inhibitory effects of compounds 1b. 2c, and 1e on phospho-Src after EGF stimulation of A431 cells measured by immuno blot. Value are expressed as area units of the corresponding gels reported in FIG. 4.

| | Control | Control + EGF[a] | PP2[a] | 1b[a] | 2c[a] | 1e[a] |
|---|---|---|---|---|---|---|
| Non-phospho-Src | 178 | 167 | 131 | 142 | 159 | 154 |
| Phospho-Src (Tyr416) | 38 | 104 | 22 | 34 | 53 | 32 |
| Phospho-Src/Non-phospho-Src ratio (%) | 21 | 62 | 17 | 24 | 33 | 21 |

[a] A431 cells treated for 15 min with 100 nM EGF.

Figure 5:
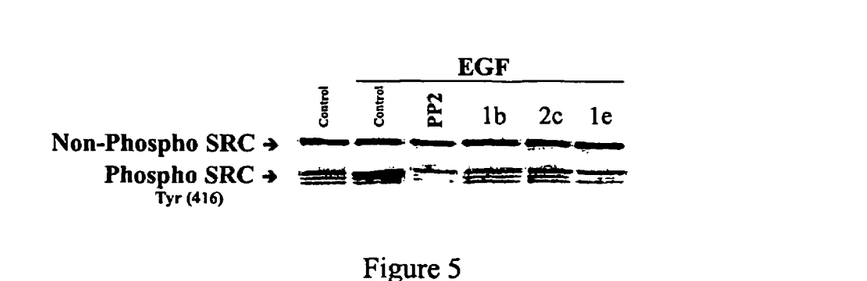
FIG. 5. Phospho-Src inhibition by compounds 1b, 2c and 1e toward A431 cells, in comparison to the reference compound PP2. Cells were cultured at a concentration of 20$^3$ cells/mL in the presence of 10 μM of the specific compound for 3 h at 37° C. EGF (0,1 μM, Cell Signaling Technology, MA, U.S.A.) was added 10 min before lysis. Cell lysates (40 μg protein) were subjected to SDS-PAGE and electrophoretically transferred to a polyvinylidene fluoride membrane. Immunoblotting was performed using the specific antibody. The membranes were visualized with luminescent substrates. The figure is a representative gel of three similar experiments.

Moreover, results from a Phospho-Src inhibition assay showed that compounds 1b, 2c, and 1e were able to inhibit Src phosphorylation with almost the same efficacy of PP2 (FIG. 5).

Reduction of Src phosphorylation is certainly one but may not be the only mechanism of inhibition of cell proliferation. We know that our compound were able to inhibit Src phosphorylation, since the latter mediates a signaling cascade leading directly to the stimulation of cell proliferation and mobility.

Finally, several compounds also showed an inhibitory effect toward the two chronic myeloid leukaemia cell lines, Meg-01 and K562, with IC$_{50}$ lower than that of the reference compound. In particular, 2c and 2d showed activity better than 50 μM.

TABLE 4

Activity data (expressed as IC$_{50}$ values) of some pyrazolo-pyrimidines toward K562 and Meg-01 cells.

| | IC$_{50}$ (μM)[a] | |
|---|---|---|
| Compd. | K562 | Meg-01 |
| 2c | 27.4 ± 0.6 | 18.1 ± 0.6 |
| 5d | 34.3 ± 0.9 | 19.4 ± 0.4 |
| 5i | 38.2 ± 0.8 | 32.7 ± 0.3 |
| 4k | 75.1 ± 1.7 | 12.1 ± 1.1 |

[a] IC$_{50}$ values are means ± SEM of series separate assays, each performed in quadruplicate.

REFERENCES

1. Chen, Y.; Thompson, W.; Semenciw, R.; Mao, Y. Epidemiology of controlateral breast cancer. *Cancer Epidemiol. Biomark. Prev.* 1999, 8, 855-861.
2. Sheffield, L. G. c-Src activation by ErbB2 leads to attachment-independent growth of human breast epithelial cells. *Biochem. Biophys. Res. Commun.* 1998, 250, 27-31.
3. Muthuswamy, S. K.; Muller, W. J. Activation of Src family kinases in Neuinduced mammary tumors correlates with their association with distinct sets of tyrosine phosphorylated proteins in vivo. *Oncogene* 1995, 11, 1801-1810.
4. Bedi, A.; Zehnbauer, B. A.; Barber, J. P.; Sharkis, S. J.; Jones, R. J. Inhibition of apoptosis by BCR-ABL in chronic myeloid leukemia. *Blood* 1994, 83, 2038-2044.
5. Endo, T.; Odb, A.; Satoh, I.; Haseyama, Y.; Nishio, M.; Koizumi, K.; Takashima, H.; Fujimoto, K.; Amasaki, Y.; Fujita, H.; Koike, T.; Sawada, K. Stem cell factor protects c-kit+ human primary erythroid cells from apoptosis. *Exp.Hematol.* 2001, 29, 833-841.
6. Huettner, C. S.; Zhang, P.; Van Etten, R. A.; Tenen, D. G. Reversibility of acute B-cell leukaemia induced by BCR-ABL1. *Nat. Genet.* 2000, 24, 57-60.

7. Lev, S.; Blechman, J. M.; Givol, D.; Yarden, Y. Steel factor and c-kit protooncogene: genetic lessons in signal transduction. *Crit. Rev. Oncog.* 1994, 5, 141-168.
8. Bondavalli, F.; Botta, M.; Bruno, O.; Ciacci, A.; Corelli, F.; Fossa, P.; Lucacchini, A.; Manetti, F.; Martini, C.; Menozzi, G.; Mosti, L.; Ranise, A.; Schenone, S.; Tafi, A.; Trincavelli, M. L. *J. Med. Chem.* 2002, 45, 4875.
9. Véliz, E. A.; Beal, P. A. *Tetrahedron Lett.* 1999, 41, 1695.
10. Giard, D. J.; Aaronson, S. A.; Todaro, G. J.; Arnstein, P.; Kersey, J. H.; Dosik, H.; Parks, W. P. *J. Natl. Cancer Inst.* 1973, 51, 1417.
11. Minafra, S.; Morello, V.; Glorioso, F.; La Fiura, A. M.; Tomasino, R. M.; Feo, S.; McIntosh, D.; Woolley, D. E. A new cell line (8701-BC) from primary ductal infiltrating carcinoma of human breast. *Br. J. Cancer* 1989, 60, 185-192.
12. Sheffield, L. G. c-Src activation by ErbB2 leads to attachment-independent growth of human breast epithelial cells. *Biochem. Biophys. Res. Commun.* 1998, 250, 27-31.
13. Hanke, J. H.; Gardner, J. P.; Dow, R. L.; Changelian, P. S.; Brissette, W. H.; Weringer, E. J.; Pollok, B. A.; Connelly, P. A. *J. Biol. Chem.* 1996, 271, 695.
14. Karni, R.; Mizrachi, S.; Reiss-Sklan, E.; Gazit, A.; Livnah, O.; Levitzki, A. *FEBS Lett.* 2003, 537, 47.
15. Maruyama, T.; Yamamoto, Y.; Shimizu, A.; Masuda, H.; Sakai, N.; Sakurai, R.; Asada, H.; Yoshimura, Y. *Biol. Reprod.* 2003, 70, 214.
16. Tatton, L.; Morley, G. M.; Chopra, R.; Khwaja, A. *J. Biol. Chem.* 2003, 278, 4847.
17. Liu, Y.; Bishop, A.; Witucki, L.; Kraybill, B.; Shimizu, E.; Tsien, J.; Ubersax, J.; Blethrow, J.; Morgan, D. O.; Shokat, K. M. S. *Chem. Biol.* 1999, 6, 671.
18. Waltenberger, J.; Uecker, A.; Kroll, J.; Frank, H.; Mayr, U.; Bjorge, J. D.; Fujita, D.; Gazit, A.; Hombach, V.; Levitzki, A.; Bohmer, F. D. *Circ. Res.* 1999, 85, 12.
19. Thomas, S. M.; Brugge, J. S. *Annu. Rev. Cell Dev. Biol.* 1997, 13, 513.
20. Gill, G. N.; Lazar, C. S. *Nature* 1981, 293, 305.
21. Mosmann, T. *J. Immunol. Method.* 1983, 65, 55.
22. Busse, D.; Doughty, R. S.; Ramsey, T. T.; Russell, W. E.; Price, J. O.; Flanagan, W. M.; Shawver, L. K.; Arteaga, C. L. *J. Biol. Chem.* 2000, 275, 6987.

The invention claimed is:

1. A compound of pyrazolo[3,4-d]pyrimidine having the formula (I)

wherein:
X=N;
R=H, alkylthio, or aminoalkylthio;
$R_1$=NHcyclopropyl, $NHC_3H_7$, $NHC_4H_9$, $N(CH_2CH_3)_2$, $NHCH_2CH_2OC_2H_5$, 1-pyrrolidinyl, 1-piperidinyl, or 4-morpholinyl, NHcyclohexyl, 1-hexahydroazepinyl, $NHCH_2C_6H_5$, or $NHCH_2CH_2C_6H_5$;

wherein $R_3$=H, halogen, or alkyl and
$R_5$=Cl, Br or OH.

2. The compound according to claim 1 wherein X=N; R=H or $SCH_3$, or $SC_2H_5$; $R_1$=$NHC_3H_7$, or $NHC_4H_9$, $N(CH_2CH_3)_2$, $NHCH_2CH_2OC_2H_5$, 1-pyrrolidinyl, 1-piperidinyl, 4-morpholinyl, NHcyclohexyl, 1-hexahydroazepinyl, $NHCH_2C_6H_5$, or $NHCH_2CH_2C_6H_5$;
$R_2$=H; $R_3$=H;

and
$R_5$=Cl, Br, or OH.

3. The compound according to claim 1 wherein X=N, R=$SCH_3$, $R_1$ is one of the following residues: $NHC_4H_9$, 1-piperidinyl, 4-morpholinyl, $NHCH_2C_6H_5$, or $NHCH_2CH_2C_6H_5$, $R_2$=H, and $R_4$=2-chloro-2-phenylethyl.

4. The compound according to claim 1 wherein X=N, R=$SC_2H_5$, $R_1$ is one of the following residues: $NHC_3H_7$, $NHC_4H_9$, or $NHCH_2C_6H_5$, $R_2$=H, and $R_4$=2-chloro-2-phenylethyl.

5. The compound according to claim 1 wherein X=N, R=H, $R_1$ is one of the following residues: $NHC_4H_9$, or NHcyclohexyl, $R_2$=H, and $R_4$=2-bromo-2-phenylethyl.

6. The compound according to claim 1 wherein X=N, R=H, $R_1$ is one of the following residues: 1-piperidinyl, or $NHCH_2C_6H_5$, or $NHCH_2CH_2C_6H_5$, $R_2$=H, and $R_4$=2-hydroxy-2-phenylethyl.

7. The compound according to claim 1 wherein X=N, R=H, $R_1$ is one of the following residues: $NHCH_2CH_2OC_2H_5$, or $NHCH_2C_6H_5$, or $NHCH_2CH_2C_6H_5$, $R_2$=H, and $R_4$=styryl.

8. A pharmaceutical composition comprising the compound of claim 1 or a pharmaceutically acceptable salt thereof, and suitable excipients.

9. A pharmaceutical composition comprising the compound of claim 2 or a pharmaceutically acceptable salt thereof, and suitable excipients.

10. A pharmaceutical composition comprising the compound of claim 3 or a pharmaceutically acceptable salt thereof, and suitable excipients.

11. A pharmaceutical composition comprising the compound of claim 4 or a pharmaceutically acceptable salt thereof, and suitable excipients.

12. A pharmaceutical composition comprising the compound of claim 5 or a pharmaceutically acceptable salt thereof, and suitable excipients.

13. A pharmaceutical composition comprising the compound of claim 6 or a pharmaceutically acceptable salt thereof, and suitable excipients.

14. A pharmaceutical composition comprising the compound of claim 7 or a pharmaceutically acceptable salt thereof, and suitable excipients.

* * * * *